(12) United States Patent
Seelig et al.

(10) Patent No.: US 7,660,698 B1
(45) Date of Patent: Feb. 9, 2010

(54) PHYTOMETRIC INTELLIGENCE SENSORS

(75) Inventors: Hans-Dieter Seelig, Boulder, CO (US); Richard J. Stoner, II, Berthoud, CO (US); Alexander Hoehn, Boulder, CO (US); William Walter Adams, III, Superior, CO (US)

(73) Assignees: Agrihouse, Inc., Berthoud, CO (US); The Regents of the University of Colorado, Denver, CO (US)

( * ) Notice: Subject to any disclaimer, the term of this patent is extended or adjusted under 35 U.S.C. 154(b) by 0 days.

(21) Appl. No.: 11/714,490

(22) Filed: Mar. 6, 2007

Related U.S. Application Data

(60) Provisional application No. 60/808,487, filed on May 25, 2006.

(51) Int. Cl.
*G01B 5/02* (2006.01)
*G01R 33/06* (2006.01)

(52) U.S. Cl. .................................... 702/170; 324/207.2

(58) Field of Classification Search ............ 702/2, 702/1, 127, 155, 156, 170, 50, 55, 57, 64, 702/65; 800/295; 324/207.2, 262, 263; 33/783; 73/29.01, 29.02, 335.02, 335.05
See application file for complete search history.

(56) References Cited

U.S. PATENT DOCUMENTS

| | | | | |
|---|---|---|---|---|
| 4,160,374 A | * | 7/1979 | Crump et al. | 73/76 |
| 4,655,076 A | * | 4/1987 | Weihe et al. | 73/73 |
| 4,768,390 A | * | 9/1988 | Baker et al. | 73/865.6 |
| 6,185,833 B1 | * | 2/2001 | Bravdo et al. | 33/783 |
| 6,397,162 B1 | * | 5/2002 | Ton | 702/136 |
| 7,412,330 B2 | * | 8/2008 | Spicer et al. | 702/2 |

OTHER PUBLICATIONS

Seelig et al., The Assessment of Water Deficit Stress in Plants Using Optical Measurement Methods, 2005, A Thesis Submitted for Ph.D. Degree, Department of Aerospace Engineering Sciences, University of Colorado.*
Manukian et al., Plant Health Sensing, Fall 1987, N89-24018, pp. 82-115.*
Mittleman et al., T-Ray Imaging, Sep. 3, 1996, IEEE Journal of selected Topics in Quantum Electronics, vol. 2, No. 3, pp. 679-692.*

* cited by examiner

*Primary Examiner*—Michael P. Nghiem
*Assistant Examiner*—Toan M Le
(74) *Attorney, Agent, or Firm*—Ruth Eure (57) ABSTRACT

Methods and apparatus for determining when plants require watering, and methods of attending to the watering of plants including signaling the grower that the plants are in need of hydration are provided. The novel methods include real-time measurement of plant metabolics and phytometric physiology changes of intrinsic physical or behavioral traits within the plant such as determining physiological flux measurement of enzyme flux due to environmental changes such as the wind and drought stress, soil and plant mineral deficiencies, or the interaction with a bio-control for organic disease control including, cell movement, signal transduction, internal chemical processes and external environmental processes including when plants require watering, and methods of attending to the watering of plants including signaling the grower that the plants are in need of hydration.

3 Claims, 4 Drawing Sheets

PHYTOMETRIC INTELLIGENCE SENSORS

CLAIM OF PRIORITY

This application claims priority from U.S. Provisional Patent Application 60/808,487, entitled "Sensor Systems and Methods for the Evaluation of Water Deficit Stress in Plants" filed May 25, 2006, which is incorporated herein by reference in its entirety.

GOVERNMENT SUPPORT

The United States government is gratefully acknowledged for partially sponsoring the research contained in this patent application under NASA Grant No. NCC8-242.

BACKGROUND OF THE INVENTION

Attending to the watering needs of plants has been an issue for mankind ever since the cultivation of plants began many thousands of years ago. The present invention provides several methods for determining when plants require watering, and methods of attending to the watering of plants including signaling the grower that the plants are in need of hydration.

Traditionally, the overall thickness of plant leaves has mostly been determined from dissected leaves under microscopes showing leaf cross-sections and including scale bars in the field of view. Although mechanical micrometers or calibers could be used for measuring the thickness of leaves, the use of mechanical micrometers or calibers is cumbersome and time consuming. In addition, the use of mechanical micrometers or calibers may damage leaf cells if the arms of the device used are closed on the leaf under investigation too forcefully during measurements.

In order to overcome the obstacles named above for measuring the overall thickness of leaves more easily and in vivo while preventing the leaf from damage, a sensor system was developed utilizing a Hall-effect sensor integrated circuit (IC), a magnet, and a gripper like fixture, which shall be denoted "Leaf Thickness Meter Utilizing a Hall-Effect Sensor" (LTMH).

It is well known that the spectral distribution of light reflected from a plant leaf differs from that of an incident beam. These spectral specifics of reflected light indicate the presence and amount of absorbers inside the leaf. The same is true for light transmitted through a plant leaf. Since leaf cells are mainly comprised of water and pigments (such as chlorophyll and carotenoids), the spectrum of light reflected from a leaf is determined to a large extent by absorption characteristics of water and pigments. In the near infrared (NIR) range, absorption by pigments becomes negligible and absorption by water becomes dominant.

The pressure that develops in leaf cells of plants due to the high elastic modulus of the walls of leaf cells and due to the presence of solutes inside leaf cells is called turgor pressure. In non-stressful situations in terms of water supply, i.e. when plants are not limited in the uptake of water, they typically regulate the turgor pressure of their leaf cells to be high. Turgor pressure in leaf cells can achieve several Mega-Pascals (MPa). Under high turgor pressure any minute change of the water content of leaf cells results in large fluctuations of turgor pressure of these cells. In fact, several studies have shown that a loss of the relative water content (RWC) of leaf cells of just 15% from their nominal high RWC-values may cause the turgor pressure of these leaf cells to decline substantially, or to be completely lost. Thus, turgor pressure of leaf cells is one of the most sensitive parameters to detect the onset of leaf dehydration. If only slight amounts of water move out of leaf cells due to the development of water deficit stress (WDS), turgor pressure typically decreases substantially in response.

If an unusual decrease of turgor pressure in leaf cells could be detected non-invasively and in real-time, such a detection could potentially signal the onset of leaf dehydration and hence the development of WDS in plants.

Traditionally, turgor pressure of cells has been determined by either one of two ways. Turgor pressure of cells has been measured by some studies directly by actually inserting microcapillary tubes into the cells under test and measuring the pressure inside the cells directly using pressure transducers or micromanometers. Clearly, such an approach is destructive, time-consuming, rather cumbersome to conduct, and mainly of academic interest. The method mostly used in practical applications determines the turgor pressure of leaf cells indirectly by determining the overall water potential ($X_w$) and the solute water potential ($X_s$) of a leaf under test by appropriate means. Since the overall water potential of leaf cells equals the sum of the solute water potential and the pressure water potential ($X_p$; which is the turgor pressure) of leaf cells:

$$X_w = X_s + X_p$$

one can easily solve the equation for the turgor pressure ($X_p$) and determine the turgor pressure once the overall water potential and the solute water potential of leaf cells are known. Various techniques for determining the overall water potential and the solute water potential of leaf cells have been described. However, all of the techniques for determining the overall water potential and the solute water potential of leaf cells are destructive as well, since all of those techniques require the taking of leaf samples for examination and all of those techniques eventually destroy those leaf samples. Furthermore, all of those techniques require the use of laboratory equipment, such as precision scales, pressure chambers, microscopes, and the like, and the determination of turgor pressure of leaf cells may take several hours or several days in order to receive final data using those methods. Thus, all of the traditional methods for the determination of turgor pressure of leaf cells may be considered destructive, time consuming, and rather difficult to conduct, and can therefore not be used for the detection of WDS in plants by monitoring turgor pressure in a leaf cell non-destructively and in real time.

The method described here overcomes the obstacles of traditional methods for determining the turgor pressure of leaf cells and measures the turgor pressure of leaf cells non-destructively, conveniently, and in real time. For doing so, the method described here utilizes the principle of "pressure broadening and shifting of spectral absorption bands".

SUMMARY OF THE INVENTION

The present invention provides several novel methods for real-time measure of plant metabolics and phytometric physiology changes of intrinsic physical or behavioral traits within the plant such as determining physiological flux measurement of enzyme flux due to environmental changes such as the wind and drought stress, soil and plant mineral deficiencies, or the interaction with a bio-control for organic disease control including, cell movement, signal transduction, internal chemical processes and external environmental processes including when plants require watering, and methods of attending to the watering of plants including signaling the grower that the plants are in need of hydration.

One novel method of the present invention includes determining the hydration needs of a plant by non-destructively measuring of phytometric physiological flux, cell movement, signal transduction, internal chemical processes and external environmental processes including the thickness of the plant leaves in vivo.

Another novel method of the present invention includes measuring the infrared light reflected from the plant leaves as a means for real-time phytometric assessing leaf water content.

A third method of the present invention includes real-time detecting plant water deficit stress by phytometric measuring the infrared light transmitted through the plant leaves as a means for assessing leaf water content and detecting plant water deficit stress.

The final method of the present invention describes a real-time phytometric method for measuring the turgor pressure of plant leaf cells non-destructively, in real time and in vivo.

All of these methods lend themselves to forming an effective plant-human interface including intelligent plant sensing and the use of internet based sensors.

The real-time phytometric invention can be extremely miniaturized. Since sensors can be manufactured very light-weight, they may be clipped onto leaves for long periods of time without disturbing the plants normal function. Data and power may be transmitted to and from these sensors wirelessly, utilizing one or several wireless data- and power-transmission technologies existing today, which are expected to be further developed and miniaturized in the near future, such as ZigBee (IEEE 802.15.4), WiFi, Bluetooth, Sensor-Mesh-Networks, and RFID.

This real-time phytometric invention provides means to measure water deficit stress in plants by using one or several of the described actual sensing methods. It also includes means to translate measured parameters into human language and to communicate with a user or operator in an intelligent way, thus fulfilling all the definitions of a smart or intelligent sensor.

For example, a base station could translate measurement parameters into voice-messages. In particular, if a device has determined that water stress is developing in a plant being measured, the device could articulate such an alarm-situation not only via lights, light-emitting-diodes, displays, buzzers, or the like, but also with an appropriate voice message.

The real-time phytometric invention could further be connected to the Internet and transmit messages and data over long distances, providing users and operators access to the intelligent leaf water stress sensors remotely and at any time. For example, the data of one or several leaf sensors could be made available on an Internet web site. This way a user/operator had access to this data worldwide wherever he/she finds access to the Internet with a computer, PDA, or cell phone. If an alarm-situation arises, i.e. if water deficit stress develops in the plants being measured, a base station could send out an email-alert, a cell phone text message, a pager message, or a cell phone voice message, thus reaching a user/operator virtually at any time. An alerted user/operator could then use any means of modern communication, such as Internet based remote communication via computer, PDA, cell phone text messaging, or cell phone voice messages, to react appropriately, for example by remotely initializing plant watering. Of course, a base station could also be used to initiate plant irrigation automatically based on the signals of leaf water stress sensors, and only alert the user/operator via the Internet or a cell phone without the need for an actual feedback from the user/operator.

The following table of elements is provided to assist in the recognition of drawing elements taken in conjunction with the accompanying drawings.

| | |
|---|---|
| 20 | Hall Effect Sensor Integrated Circuit |
| 22 | magnet |
| 24 | Gripper like fixture |
| 26 | Leaf |
| 30 | Housing |
| 32 | 1450 nm LED |
| 34 | 1300 nm LED |
| 36 | IR Photodiode Sensing Element |
| 38 | Aperture |
| 40 | Black Absorbing Background Material |
| 50 | Upper Housing |
| 52 | 1450 nm LED |
| 54 | 1300 nm LED |
| 56 | Lower Housing |
| 59 | IR Photodiode Sensing Element |
| 60 | Aperture |

DETAILED DESCRIPTION OF THE INVENTION

The following definitions are provided to clarify the invention:

Physiological Bio-Feedback

The plant physiological biofeedback associated with the measurement of intrinsic physical or behavioral traits within the plant as described in this invention. These traits are measured in real-time. The bio-feedback signal is measured in a unit yet to be determined, at this point termed "plant-stress". The bio-feedback analog or digital signal is stored in the RAM of a computer chip. The plant is said to reach the unit "plant-stress" when the data spikes. For example, it has been shown that the TIR leaf water index as described in this invention exhibits a characteristic increase between several hours and several days before leaves actually start to dehydrate during the development of water deficit stress. It is our believe that this phenomenon is a direct result of the relocation of chloroplasts within cells due to the down-regulation of photosynthetic activity. Thus, the described characteristic increase of the TIR leaf water index may be used to detect the down-regulation of photosynthetic activity easily, non-destructively, and in real-time. Detecting the down-regulation of plant-photosynthetic activity easily, non-destructively, and in real-time, provides an advantageous bio-feedback signal for plant cultivation since at the point in time where photosynthesis is down-regulated due to the influence of stressful environmental conditions, such as water deficit stress, no sign of stress or desiccation is typically visible to visual inspection of a plant by the unaided eye. Such bio-feedback signals are therefore far more advantageous compared to plain visual inspections of plants in terms of detecting detrimental environmental conditions early, or actually in real-time. The biofeedback methods described in this invention also have an economic advantage compared to currently available typical measurement equipment for the assessment of plant photosynthetic activity based on carbon-dioxide flux, stomatal conductance, or leaf temperature. Such measurement equipment, typically termed "photosynthesis suites", are usually rather expensive, and have so far gained market potential in academic applications mainly. In contrast, the bio-feedback methods described in this invention have the potential to be manufactured rather inexpensive and can be operated fully automatically over longer periods of time under actual field conditions, such as in farming or greenhouse applications.

Physiological Flux

The Apogee Instruments BQM (basic quantum meter) manufactured by Apogee Instruments Logan, Utah, measures the photosynthetic photon flux of a light source. The BQM measures and calculates the amount of energy in the light source necessary for plant photosynthesis. NASA has determined the level of photon flux for a number of vegetables and fruiting plants (Stoner, NAS10-98030).

Photon flux of either sunlight or electrical is measured in units of $\mu mol \cdot m^{-2} \cdot s^{-1}$). The user points BQM towards the light source and the photon flux is read out on the digital meter. The Apogee Instruments BQM is not a phytometric device. It is a real-time light source-measuring device. A plant is not required to be present when using the device.

Our invention differs vastly from the BQM device. During the photosynthetic processes chloroplasts can be said to be in a real-time state of flux. When light is present the chloroplasts gather inside the cell and arrange themselves at the top and bottom axis of the cell. As the light source becomes weaker (ie. the sunset), or becomes excessive of what can be used for photosynthesis but rather might result in photodamage, the chloroplasts move and gather along the sides of the plant cells (away from the axis). This chloroplast gathering is reversed when light appropriate for photosynthesis is present (ie. sunrise). This type of physiological flux is an intrinsic physical or behavioral trait within the plant. The present invention comprises a device which to measure intrinsic physical or behavioral traits of a plant physiological flux in real-time.

Other examples of real-time phytometric flux is the measurement of enzyme flux due to environmental changes such as wind and drought stress, soil mineral deficiencies, or the interaction with a bio-control for organic disease control (U.S. Pat. No. 6,193,988). Another example of the invention is the measurement of turgor pressure.

Cell Movement

Plant cell movement refers to morphological changes of leaf cell arrangements due to fluctuations in turgor pressure. The invention comprises a phytometric device capable of measuring cell movement such as described under the turgor pressure measurement method within the body of this document.

Signal Transduction

Plant cell signal transduction as disclosed in U.S. Pat. No. 6,193,988 describes the physiological processes that elicit enzyme activity. The present invention comprises a phytometric device for measuring signal transduction.

Internal Chemical Processes

Mineral uptake as described by Stoner and Linden (2006) are an example of internal chemical processes. An example is the Ca ion exchange that takes place when a bio-control containing elicitor described by Stoner and Linden (2006) are in direct contact with the plant cell wall. The ion exchange direct is absorbed by the cell and assimilated into the plant. The invention comprises a phytometric device capable of measuring internal chemical processes including Ca ion, nitrogen, phosphate, potassium, iron, sulfur and other trace elements.

External Environmental Processes

The measurement of physiological flux with a phytometric device for measuring wind and drought conditions are examples of external environmental processes as they relate directly to the cells of the plant. Another example of an external environmental process is the phototrophic response of a plant bending towards a light source placed near the side of the plant. The plant bends because more light is on one side of the plant. The bending is due to an increase of photosynthetic process within the plant cells. In such case the plant appears to bend away for the dark.

The invention comprises a phytometric device which measures pathogen and insect pressures within the local environment, such as a field. The real-time measure of external environmental processes would provide a phytometric biofeedback signal of plant pathogen response such as the dying back of cells where pathogen infection occurs.

Means for Generating a Signal

A phytometric biofeedback real-time signal is generated using discrete sensory devices combining magnetic resistance radio frequency and infrared technology for plant intelligence as described in this invention. These are alternatives to current technologies of soil-based moisture monitoring and aerial infrared imaging.

Means for Transmitting a Signal

The "Sg-1000™," based on research conducted at the University of Colorado at Boulder, provides real-time leaf sensor RFID signaling of field crops, transmitted using 802.11b/g wireless network protocols to WiFi industrial systems (I/O), which then control mechanical or solid state electronic hardware used for plant sustainable inputs such as water. Control could be realized by mechanical or solid state electronic hardware such as irrigation gates, pumps, solenoids, alarms, or other means, such as system features.

Means for Receiving a Signal.

The signal transmitted by the Sg-1000™ is received in real-time by a WiFi router (802.11b/g wireless networks) such as those found in many business and homes today.

Methods of the Present Invention

Method 1: Measuring the overall thickness of leaves may be necessary or useful in order to correct the measurement of infrared light reflected from or transmitted through leaves qualitatively correct to the relative water content (RWC) of leaf cells as means to assess the water content of leaves or plant water deficit. Leaf water content indices utilizing a dual wavelength method, such as the ratio of leaf reflectance at 1300 nm divided by leaf reflectance at 1450 nm, can be easily shown to correlate qualitatively closely to the RWC of leaf cells. The RWC of leaves decreases substantially during leaf dehydration, which is the final phase of water deficit stress (WDS) in plants. Thus, if the RWC of leaf cells could be estimated using light reflected from leaves, the detection of a substantial loss of the RWC of leaf cells from nominal values may be used for the detection of WDS in plants.

However, leaf water content ratios based on light reflected from or transmitted through leaves are not only a function of the RWC of leaf cells. The overall thickness of leaves influences such ratios as well. The reason for this dependency is that leaf water content ratios based on light reflected from or transmitted through leaves are primarily a function of the absolute amount of water perceived by the light reflected from or transmitted through leaves, which may be approximated by the so-called equivalent water thickness (EWT) of leaves. This absolute amount of water, however, depends on two factors: the overall developed thickness of leaves and the RWC of leaf cells. Thus, in order to estimate the RWC of leaf cells using light reflected from or transmitted through leaves, the overall thickness of theses leaves has to be taken into account in order to convert such leaf water content ratios based on reflectance or transmittance qualitatively correct to the RWC of leaf cells, which creates the need to measure the overall thickness of leaves conveniently, with high resolution, non destructively, and in real-time.

The results of recent studies investigating the dynamics of leaf parameters during the development of water deficit stress in plants have pointed to another application calling for the need to measure the overall thickness of leaves conveniently, with high resolution, non-destructively, and in real time. The results of these studies indicate that the overall thickness of leaves may be used to indirectly detect the loss of turgor pressure of leaf cells, hence the onset of leaf dehydration. The turgor pressure of leaf cells is one of the most sensitive parameters to detect the onset of leaf dehydration. Thus, if the substantial decrease of turgor pressure in leaf cells could be detected non invasively and in real-time, such a detection could potentially signal the onset of leaf dehydration and hence the development of WDS in plants.

Unusual decline of the overall thickness of leaves may indicate the substantial reduction or loss of turgor pressure of leaf cells which in turn may signal the onset of leaf dehydration as it may happen during the development of WDS in plants. Hence, the detection of unusual declining leaf thicknesses may be used for the detection of WDS in plants, which calls for the need to measure the overall thickness of leaves conveniently, with high resolution, non destructively, and in real-time, as realized by the developed LTMH leaf thickness sensor.

Figure 1:
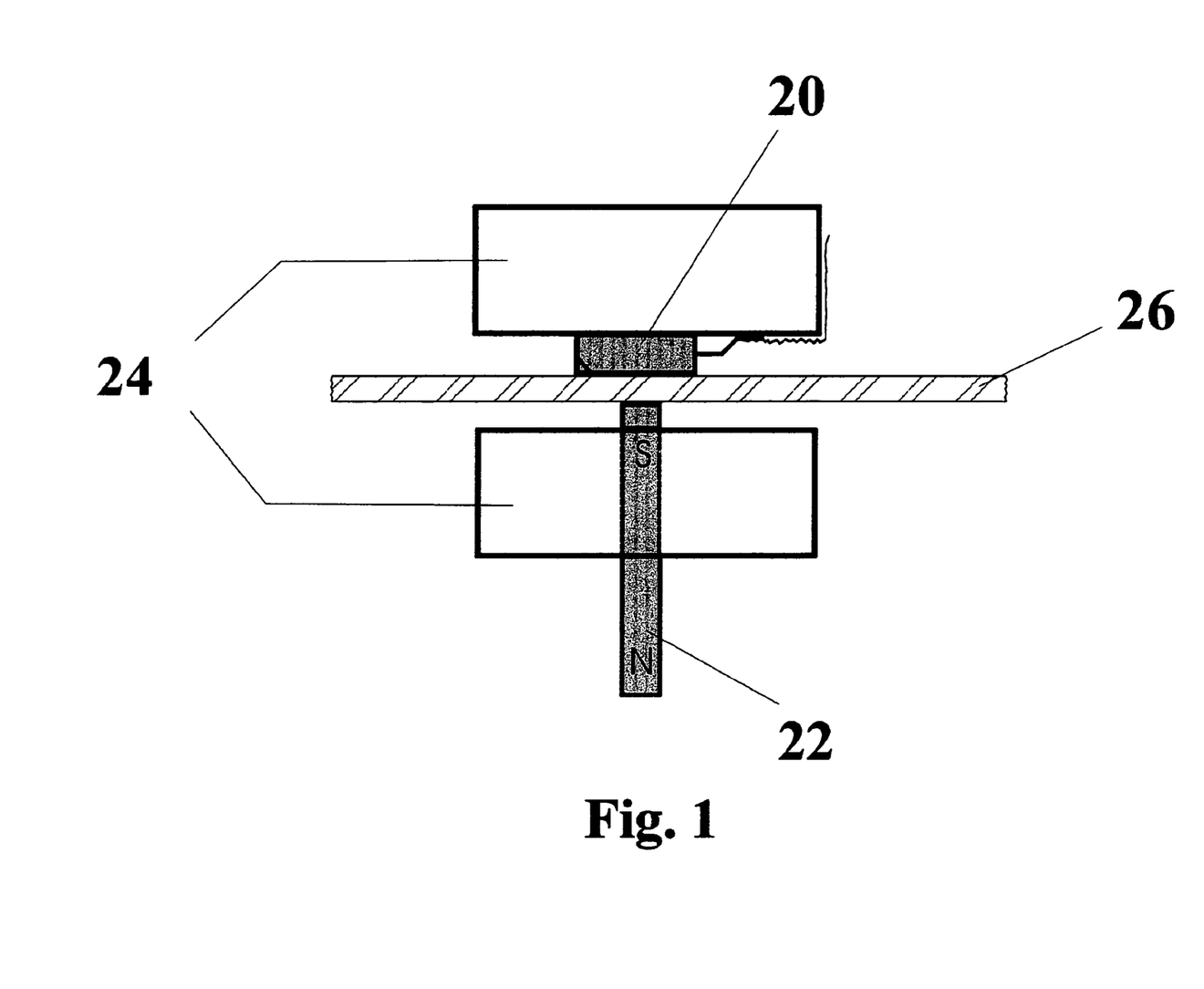
FIG. 1 is a schematic drawing showing the elements of the plant leaf thickness sensor.

Please refer to FIG. 1. The apparatus of the present invention comprises a sensor system known as a LTMH sensor. The instant system currently contains a Hall-effect sensor Integrated Circuit (IC) 20 with analog signal output (model MLX90215, Melexis Microelectronic Systems, Concord, N.H.) and a magnet 22 (model HE155, Hamlin Electronics, Lake Mills, Wis.). The magnetic sensitivity of the used Hall-effect sensor IC MLX90215 was programmed to be 20 mV/mT, the output voltage of this Hall-effect sensor IC 20 when no magnetic flux is present ($V_{out}$@B=0) was programmed to be 2.5 V, and the used magnet HE155 exhibits a nominal magnetic flux density of 12.0 mT (120 Gauss). Both elements, the Hall-effects sensor IC 20 and the magnet 22, are mounted on a gripper like fixture, such as gripper arms 24, for example, in such a way that they can touch a leaf 26 from opposite sides.

The Hall-effect sensor IC 20 measures magnetic flux density and converts this measurement into a corresponding voltage, the so-called Hall-voltage. Since both elements are mounted on gripper like fixture 24, their positions with respect to each other are fixed, except that the distance between the magnet 22 and the Hall-effect sensor IC 20 can be varied by opening and closing movements of the arms of the gripper like fixture 24. Thus, the magnetic flux density perceived by the Hall-effect sensor IC 20 depends on the distance between the Hall-effect sensor IC 20 and the magnet 22 only. Hence, when this gripper fixture 24 is clipped onto a leaf 26 and the arms of the fixture 24 are allowed to close, the final distance between the Hall-effect sensor IC 20 and the magnet 22 is given by the thickness of the leaf 26 under test, resulting in the Hall-voltage to be a function of the leaf thickness.

The gripper like fixture 24 not only provides the exact positioning of the Hall-effect sensor IC 20 and the magnet 22 with respect to each other, but also allows the convenient operation of this LTMH-sensor system when measuring the thickness of leaves as a clip-on-leaf type sensor. The closing force of this fixture is currently provided by 1 inch thick OPENCELL-foam (model 30100, Future Foam, Inc., Denver, Colo.) mounted between the arms of the gripper like fixture 24 at the end opposite of the Hall-effect sensor IC 20 and the magnet 22, so that this LTMH-sensor system can be closed on a leaf 26 extremely gently, avoiding the problems of damaging leaf cells often associated with conventional mechanical micrometers or calibers, although other means for providing a gentle closing force could be applied as well.

The magnet 22 used is cylindrical in form with a diameter of about 3 mm. If the gripping fixture 24 is clipped onto a leaf so that the magnet 22 is positioned at the abaxial (lower) side of the leaf 26, the magnet 22, due to its small diameter, typically fits between major leaf veins, thus allowing the measurement of the thickness of leaves at typical leaf cross sections without the misleading effect of major veins.

When the gripper like fixture 24 is completely closed without any material present between the Hall-effect sensor IC 20 and the magnet 22, i.e. if the Hall-effect sensor IC 20 and the magnet 22 touch each other, the output voltage of the Hall effect sensor IC has been measured to be about 4.2 V. This particular Hall-voltage shall be denoted "zero position Hall voltage" for calibration purposes.

In order to calibrate the LTMH-sensor, a stack containing 20 sheets of writing paper and 4 sheets of plastic foil was created. Each sheet of writing paper exhibited a sheet-thickness of about 100 μm and each sheet of plastic foil exhibited a sheet-thickness of about 25 μm. This stack was used to create various calibration thicknesses by combination of various numbers of writing paper and plastic foil, which were measured with the developed LTMH-sensor and immediately verified using a mechanical micrometer (Micrometer No. 616, Brown & Sharp Mfg. Co., Providence, R.I.). During the calibration process a certain number of writing papers and plastic foils was placed between the arms of the LTMH sensor, the arms of the LTMH-sensor were allowed to close, the output voltage of the LTMH-sensor was recorded, as well as the corresponding control measurement of the created thickness of writing papers and plastic foils using the mechanical micrometer, for each thickness investigated.

The relationship between the Hall-voltage difference to the "zero position Hall voltage" and applied distances, or thicknesses, appeared to be a polynomial function of second degree, exhibiting a coefficient of determination ($R^2$) of greater than 0.999. Thus, the principle described above appears to be an accurate and convenient way to measure the thickness of plant leaves. The calibration procedure described above can be justified because the absolute magnetic permeability of water is close to the absolute magnetic permeability of air, or vacuum, which is why the relative permeability of water is close to one. Thus, the difference between determining the thickness of plant leaves, the cells of which are mainly comprised of water, and the thickness of sheets of writing paper and plastic foil, can be assumed to be negligible. In fact, when the LTMH-sensor was applied to real leaves, using the calibration formula as obtained in the calibration process described above, and these measurements were verified using a mechanical micrometer, virtually no difference was found between the results in leaf thickness obtained using the LTMH-sensor, and using the mechanical micrometer.

The LTMH-sensor currently exhibits a resolution of about 0.5 μm and a repeatability of measurement results of smaller than about 10 μm. Updating the "zero position Hall voltage" may decrease the repeatability below about 5 μm. The developed LTMH-sensor is connected to appropriate electronics (stand-alone or in conjunction with a computer or a computer alone), which provides appropriated control, particularly reading of the output voltage of the Hall-effect sensor at appropriate times, signal conditioning, and data display and storage.

Before measurements are to be taken from leaves, the electronics or computer software records and stores the "zero position Hall voltage" ($V_{Hall\_0}$), i.e. the output voltage of the Hall-effect sensor IC when no leaf is present between the Hall-effect sensor IC and the magnet and the fixture is completely closed (Hall-effect sensor IC touches the magnet).

During actual measurements, i.e. with a plant leaf 26 placed between the Hall-effect sensor IC 20 and the magnet 22 while the gripping fixture 24 is allowed to close on the leaf 26, the electronics or computer software records and stores the measured Hall-voltage ($V_{Hall\_leaf}$), calculates the "Hall-voltage difference to zero position" ($V_{Hall\_diff}$) according to the formula:

$$V_{Hall\_diff} = V_{Hall\_leaf} - V_{Hall\_0}$$

and calculates the corresponding leaf thickness (LT) in micrometers of the leaf under test.

Method 2: The described sensor-system measures infrared light at specific wavelengths reflected from plant leaves as a way to assess leaf water content and to detect plant water deficit stress. The described sensor defines a variety of measurement parameters and keeps those parameters constant. Doing so reduces data variability to acceptable levels and provides means for assessing leaf water content fruitfully. Specific signatures of leaf water content indices based on light reflected from leaves can indicate the dehydration of leaves in real-time.

Pure water exhibits 5 main absorption bands in the NIR light range, centered at about 970 nm, about 1200 nm, about 1450 nm, about 1930 nm, and at about 2500 nm. These 5 main water absorption bands in the NIR can typically be observed in the form of reflectance-troughs when assessing light reflected from leaves. If leaves dehydrate, for example due to prolonged water deficit stress, the above named reflectance-troughs typically tend to decrease with increasing dehydration of the leaves. The application of a dual wavelength method utilizing one of the above named water absorbing bands in the NIR, i.e. measuring leaf reflectance at a water absorbing wavelength and at a non (or weakly) absorbing wavelength and dividing the non-(or weakly) absorbing wavelength by the absorbing wavelength, can be used to determine the depth of the corresponding water absorption trough in the reflectance spectrum. Applying a dual wavelength method utilizing the 1450 nm water absorbing wavelength and the 1300 nm non (or weakly) water absorbing wavelength for light reflected from peace lily (*Spathiphyllum lynise*) leaves exhibiting various degrees of leaf dehydration as characterized by the relative water content (RWC) of those leaves can be observed. Plotting the ratio of leaf reflectance at 1300 nm (R1300) divided by leaf reflectance at 1450 nm (R1450) versus the RWC of the leaves investigated, which is often used to describe the water status of a leaf under test, showed a significant correlation that appeared to be linear exhibiting a coefficient of determination ($R^2$) of greater than 0.94. Therefore, the application of such a dual wavelength ratio utilizing a water-absorbing wavelength when examining leaf reflectance may be used to assess the degree of leaf hydration, and such a dual wavelength ratio may be referred to as reflectance based leaf water index (RWI).

However, even though it is easy to correlate RWI, such as R1300/R1450, to the RWC of leaves, the true independent variable governing such a leaf water index based on reflectance is the absolute amount of water within a leaf, not the RWC of leaf cells. More specifically, such a leaf water index based on reflectance depends on the absolute amount of water encountered by light along its path when such light penetrates a leaf under test and is reflected from this leaf.

It is generally understood that light is not simply reflected at leaf surfaces as specular reflection. Although a small percentage of light incident to the adaxial (upper) side of a leaf may be specularly reflected at the leaf surface (cuticle), the majority of such incident light will penetrate the leaf, which can be shown by applying Fresnel's equations and assuming an index of refraction of 1.42 for typical leaf cell walls, as well as an index of refraction of 1.00 for air. Upper epidermal cells commonly focus incident light into the cells of the palisade layer based on their planoconvex shape. Cells of the palisade layer typically guide light straight towards the layer of spongy mesophyll cells because of total inner reflection. The layer of mesophyll cells, consisting of irregularly shaped cells and a high proportion of intercellular air spaces, intensely scatters and reflects light, mainly at cell wall-to-air interfaces due to the jump in the refractive index, eventually causing some light to be reflected back through the adaxial side of the leaf. Therefore, reflection in leaves occurs mainly at the layer of spongy mesophyll cells, and the majority of light reflected from leaves emanates from the interior of the leaf as diffuse reflection.

The exact path of light reflected from leaves depends on a variety of factors, such as anatomical specifics, the sizes and shapes of cells and their specific arrangements, and the status of cell-turgidity, which is why the exact path of light reflected from leaves can hardly be predicted or described. On the one hand, light reflected from leaves does not have to travel through the entire thickness of these leaves since it is likely reflected somewhere at the leaf interior. On the other hand, light reflected from the adaxial side of leaves has traveled through the layer of palisade cells twice, thus experienced the absorber amount of water of this cell layer 2 times.

The absolute vertical amount of water throughout a leaf cross section may be approximated by the so-called equivalent water thickness (EWT) of leaves. Although the exact path-length of light reflected from leaves may be different from the overall thickness of these leaves, as well as different from the EWT of these leaves, leaf water indices based on reflectance can typically be correlated closely to the EWT of these leaves. The spectral separation of light necessary for the above-described method can be achieved by several means. In traditional solutions for spectral separation of light a spectrally broadly emitting light source is used as illumination source, such as the sun or light bulbs. Spectral separation of light into wavelengths of interest is than achieved by applying specific spectral filters in front of receiving/sensing elements, or by applying various techniques for more complete spectral analysis, such as by splitting light into the spectrum utilizing prisms, gratings, and similar means.

Another technique of spectral separation of light in spectral analysis of matter is to apply light sources emitting only at wavelengths of interest, such as lasers or light emitting diodes (LED's), which is used by this invention. The sensor described here can be used for the measurement of the "Reflectance in the Infrared Based Leaf Water Index" (RIR-water index or RIRWI) and shall be denoted "RIRWI-Sensor".

Figure 2:
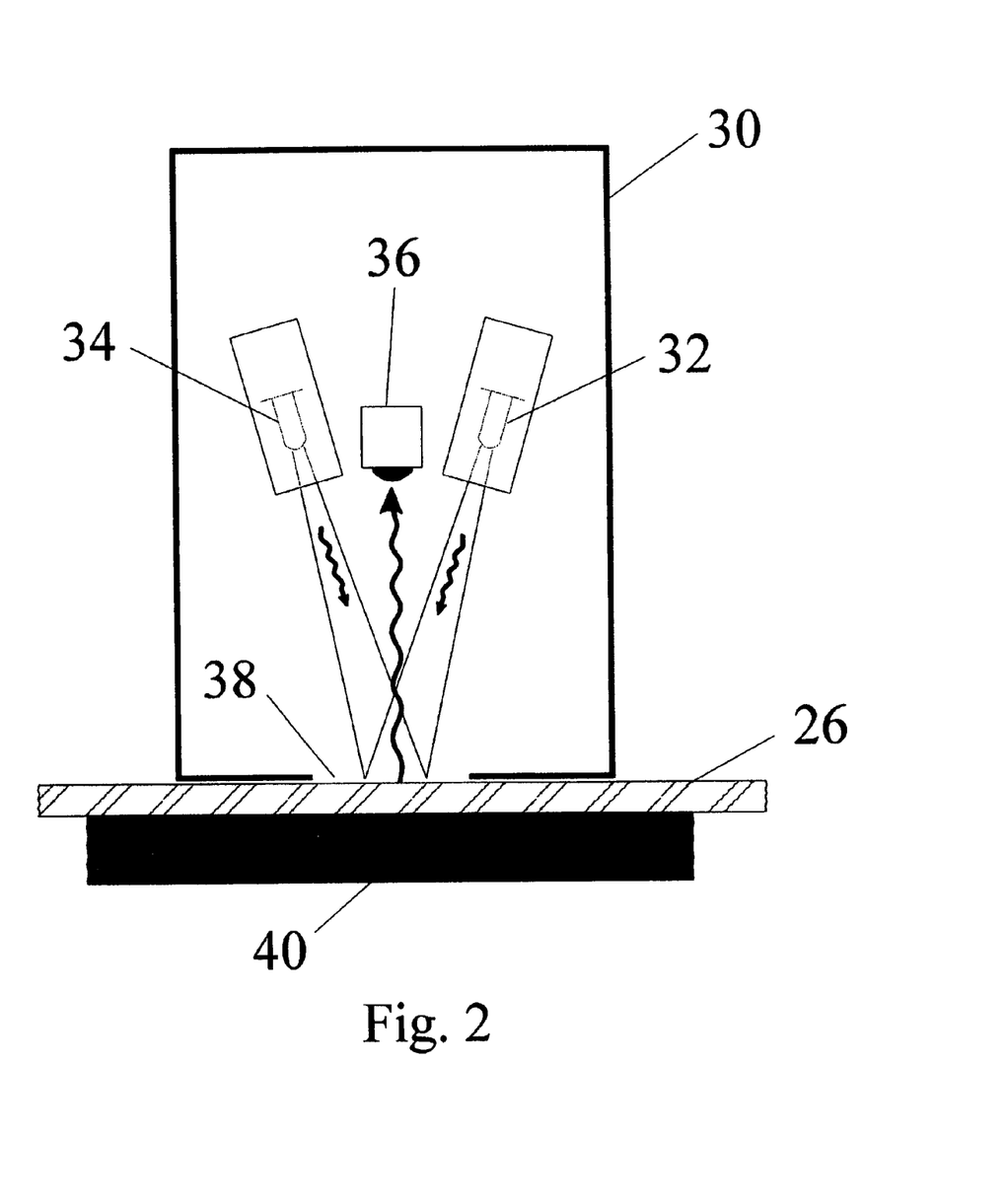
FIG. 2 is a schematic drawing showing the elements of the Reflectance in the Infrared Based Leaf Water Index, denoted "RIRWI-Sensor."

Please refer to FIG. 2, which depicts RIRWI-sensor. The RIRWI-sensor housing 30 contains the illumination sources 32, 34 (LEDs) and the sensing element (IR-photodiode). Two LED's were used as illumination sources. LED 32 emits light at the chosen water absorbing wavelength of 1450 nm, having a bandwidth of about 100 nm (FWHM) (model L1450-03, Epitex Inc., Kyoto, Japan). The second LED 34 emits light at the non (or weaker) water absorbing wavelength of 1300 nm, having a bandwidth of about 100 nm (FWHM) (model L1300-03, Epitex Inc., Kyoto, Japan). Hence, the spectra of the light beams emitted from LEDs 32, 34 are separated from each other in order to provide a clear separation between water absorbing wavelength and non (or weaker) water absorbing wavelength. An InGaAs photodiode (model PD1300-35T00, Epitex Inc., Kyoto, Japan) serves as sensing element 36 (IR-photodiode), which is responsive within the 800-1700 nm range.

All three main elements, both LED's 32, 34 and the IR-photodiode sensing element 36, are positioned in one housing 30 facing a common aperture 38 at one end of the housing, which is currently circular having a diameter of about 10 mm, for example. Both LED's 32, 34 are optically shielded at their sides so that they can only illuminate the housing aperture but are unable to illuminate the IR-photodiode sensing element 36 directly. Therefore, when this sensor system is placed on a leaf 26 with its aperture, the IR-photodiode sensing element 36 measures light that is reflected from the leaf 26, which originates from the LED's 32, 34.

The sensor system is mounted on a gripper like fixture (not shown), similar to the gripper like fixture 24 of the previous method, allowing the convenient operation of this sensor system as clip-on-leaf type sensor since the gripper like fixture 24 provides a closing force. Also, the gripper like fixture ensures that a leaf under test is always forced to be placed right at the aperture 38 of the sensor housing 30 during measurements, thus always ensuring specific viewing geometries and orientation of the leaf under test with respect to the illumination sources (LEDs) 32, 34 and the sensing element IR-photodiode 36. Furthermore, this fixture may provide defined background properties can be designed to house appropriate background materials. Black light absorbing material 40, such as black antistatic foam, may be used to provide black absorbing background properties. Black sealing foam may be used around the housing aperture, i.e. where the fixture touches the leaf, in order to provide optical shielding from ambient light.

The illuminating LEDs 32, 34 and the IR-photodiode sensing element 36 are connected to appropriate electronics (stand-alone or in conjunction with a computer or a computer alone), which turns the LEDs 32, 34 on and off in proper sequences and conducts the readout of the IR-photodiode sensing element 36 at appropriate times. Therefore, if the fixture is clipped onto a leaf, and one of the LEDs 32, 34 is turned on, emitting light at its specific wavelength, this light will penetrate the leaf under test. Some of this light will be reflected back from the leaf and may be received by the IR-photodiode sensing element 36 as reflectance.

Before measurements are to be taken from leaves, the electronics records and stores the reflected standard photon fluxes of both LED's ($I_{r\_s}$), i.e. the photon fluxes of this sensor system reflected by a hydrophobic white highly diffuse reflecting reflectance standard (no leaf placed at the sensor housing aperture).

During actual measurements, i.e. with a plant leaf placed at the sensor housing aperture, the electronics records and stores the measured photon fluxes for each of the LEDs when they are turned on ($I_{r\_leaf}$) and calculates the reflectance (R) for each LED according to the formula:

$$R = I_{r\_leaf}/I_{r\_s}$$

thus yielding R1300 and R1450 values. The RIR-water index (RIRWI) is finally calculated by the formula:

$$RIRWI = R1300/R1450$$

Dark signals, i.e. the signal measured by the IR-photodiode when no LED is turned on, may be recorded and stored for further signal conditioning purposes, or in order to detect inappropriate shielding.

Method 3: Measuring infrared light at specific wavelengths transmitted through plant leaves is a tool for assessing leaf water content and detection of plant water deficit stress.

The described sensor-system measures infrared light at specific wavelengths transmitted through plant leaves as a way to assess leaf water content and to detect plant water deficit stress. The described sensor defines a variety of measurement parameters and keeps those parameters constant. Doing so reduces data variability to acceptable levels and provides means for assessing leaf water content fruitfully. Specific signatures of leaf water content indices based on light transmitted through leaves can indicate the dehydration of leaves in real-time, and can even signal water deficit stress before any sign of water deficit becomes apparent to visual inspection by the unaided eye.

Due to the nature of light being a combination of transmitted, absorbed and reflected light, what was stated earlier regarding reflected light, largely holds true for transmitted light. As mentioned earlier, the 5 main absorption bands in the NIR light range, centered at about 970 nm, about 1200 nm, about 1450 nm, about 1930 nm, and at about 2500 nm can typically be observed in the form of transmittance-troughs when assessing light transmitted through leaves. If leaves are dehydrated, for example due to prolonged water deficit stress, the above named transmittance-troughs typically tend to decrease with increasing dehydration of the leaves. The application of a dual wavelength method utilizing one of the above named water absorbing bands in the NIR, i.e. measuring leaf transmittance at a water absorbing wavelength and at a non (or weakly) absorbing wavelength and dividing the non-(or weakly) absorbing wavelength by the absorbing wavelength, can be used to determine the depth of the corresponding water absorption trough in the transmittance spectrum. Therefore, the application of such a dual wavelength ratio utilizing a water-absorbing wavelength when examining leaf transmittance may be used to assess the degree of leaf hydration, and such a dual wavelength ratio may be referred to as transmittance based leaf water index (TWI).

However, the true independent variable governing such a leaf water index based on transmittance is the absolute amount of water within a leaf, not the relative water content (RWC) of leaf cells that is often used to describe the water status of a leaf under test. More specifically, such a leaf water index based on transmittance depends on the absolute amount of water encountered by light along its path through a leaf under test. The absolute vertical amount of water throughout a leaf cross section may be approximated by the so-called equivalent water thickness (EWT) of leaves. The exact path of light transmitted through leaves depends on a variety of factors, such as anatomical specifics, the sizes and shapes of cells and their specific arrangements, and the status of cell-turgidity.

Yet, leaf water indices based on transmittance can be shown to correlate closely to the EWT of leaves. Leaf water index based on transmittance utilizing the strongly water absorbing wavelength at 1450 nm and the non (or weakly) water absorbing wavelength at 1300 nm versus the EWT of cowpea (*Vigna unguiculata* (L.) Walp.) leaves can be observed. This particular dual wavelength ratio "transmittance at 1300 nm" divided by "transmittance at 1450 nm" (T1300/T1450) shall be denoted "Transmittance in the Infrared Based Leaf Water Index" (TIR-water index or TIRWI). In order to create different EWT of the leaves examined different cowpea plants were cultivated under different light conditions but the same other cultivation conditions, such as temperature, humidity and fertilization, including sufficient irrigation.

Leaf water indices based on transmittance depend on one hand on the developed thickness of leaves, which in turn governs the resulting leaf-EWT, and on the other hand on the relative water status of a plant under test, which may be described by the RWC of leaves affecting the EWT of leaves as well. If leaves dehydrate, for example due to prolonged water deficit stress, leaf water indices based on transmittance will decrease accordingly because of the reduction of the total amount of absorbing water along the path of light transmitted through a leaf under test, but originating from a baseline-value corresponding to the developed leaf thickness in a well watered situation.

Investigating the dynamics of the TIR-water index over the time course of prolonged water deficit stress (WDS) confirmed the conclusions drawn above. As the cowpea leaves dehydrated, the TIR-water index decreased dramatically. More importantly, the TIR-water index increased substantially compared to its well-watered value in cowpea leaves at least 14 hours before the leaves actually started to dehydrate.

While the decrease of the TIR-water index during leaf dehydration can be explained by decreasing total amounts of the absorbing water along the path of light transmitted through leaves, the observed increase of the TIR-water index between several hours and several days before the onset of actual leaf dehydration in both cowpea leaves and sugarbeet leaves appears to be a sign of the down-regulation of photosynthesis.

One hypothesis trying to explain the observed increase of the TIR-water index between several hours and several days prior to the onset of actual leaf dehydration reasons that this phenomenon may by caused by the movement of chloroplasts in leaf cells. Indeed, it has been shown that under low light conditions chloroplasts are typically moved to periclinal cell walls (top/bottom of cells) gathering side-by-side perpendicular to the direction of incident light. This movement is called accumulation movement of chloroplasts and is thought to harvest light as efficiently as possible in order to maximize photosynthesis. When photon flux rates are in excess of what is required for photosynthesis, chloroplasts move away from light beams, typically gathering along anticlinal cell walls (sidewalls of cells) parallel to the direction of incident light. The later movement is known as avoidance movement of chloroplasts and appears to minimize potential photodamage to the photosynthetic machinery. However, when chloroplasts are moved from periclinal cell walls to anticlinal cell walls when switching to avoidance mode, the volume originally occupied by chloroplasts at periclinal cell walls is replaced with cytosol, which is mainly water. Therefore, an increase in the TIR-water index may be a direct result of leaves switching from accumulation mode to avoidance mode of chloroplast movement, since in avoidance mode more absolute amount of water is present in the path of light transmitted through leaves. Indeed, even if light regimes do not change, the down-regulation of photosynthesis due to stressful reasons, such as water deficit stress, may cause leaf cells to switch from accumulation mode to avoidance mode of chloroplast movement, since a photon flux rate considered low light condition for up-regulated photosynthetic activity may be considered a high light condition, or excessive of what can be used by photosynthesis, for down-regulated photosynthetic activity. Thus, the observed typical increase of the TIR-water index may be a sign of the down-regulation of photosynthetic activity due to stressful environmental conditions, such as prolonged water deficit stress.

Figure 3:
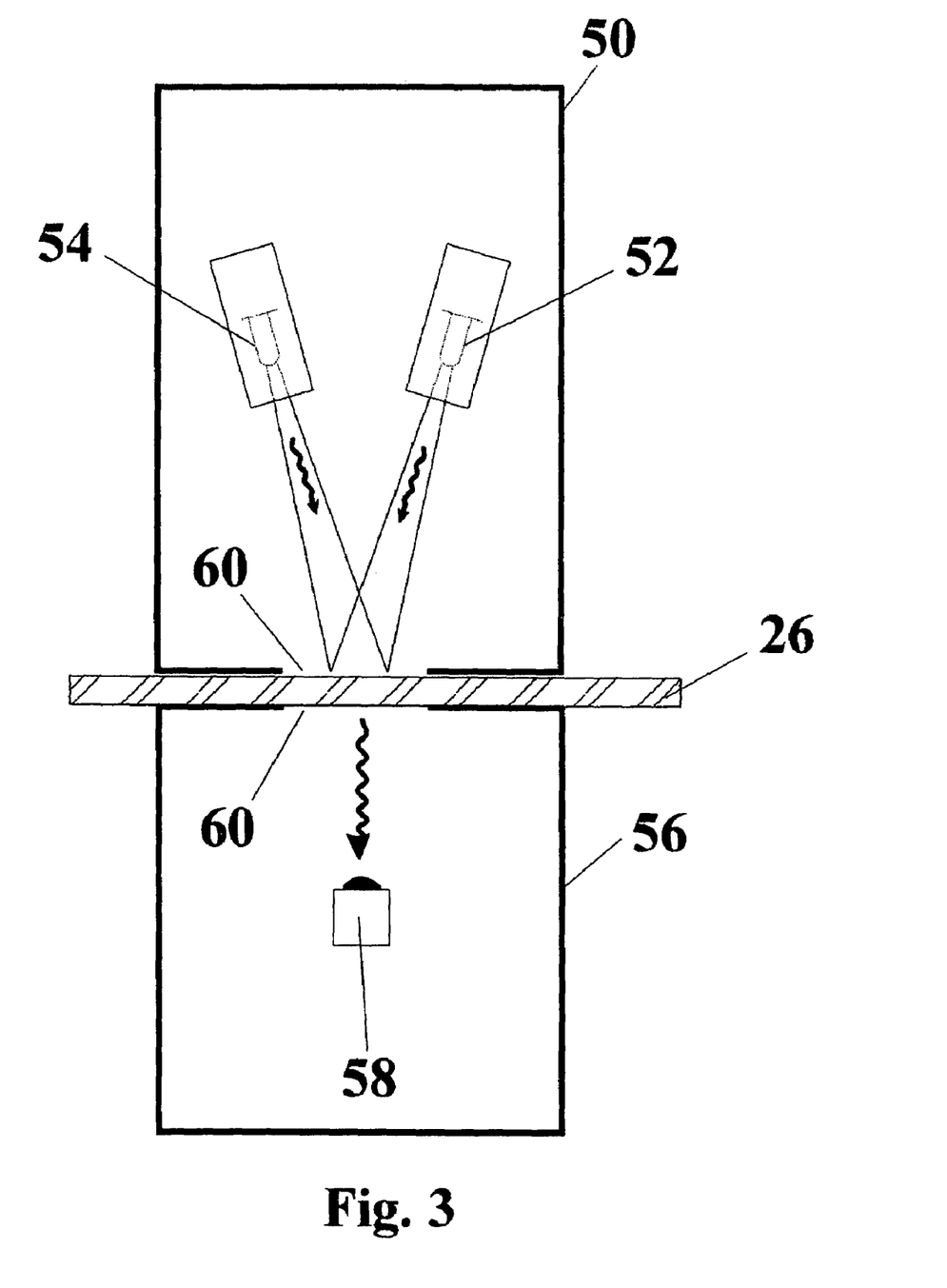
FIG. 3 is a schematic drawing showing the elements of the Transmittance in the Infrared Based Leaf Water Index, denoted the "TIRWI Sensor."

Please refer to FIG. 3. Spectral separation of light in spectral analysis of matter an be achieved by applying light sources emitting only at wavelengths of interest, such as lasers or light emitting diodes (LED's), which is used by this invention. The sensor invented here can be used for the measurement of the "Transmittance in the Infrared Based Leaf Water Index" shall be denoted "TIRWI-Sensor".

The TIRWI-sensor contains two parts: an upper housing 50 containing the illumination sources (LEDs) 52, 54, and a lower housing 56 containing the sensing element IR-photodiode 58. Two LED's were used as illumination sources. One LED 52 emits light at the chosen water absorbing wavelength of 1450 nm, having a bandwidth of about 100 nm (FWHM) (model L1450-03, Epitex Inc., Kyoto, Japan). The second LED 54 emits light at the non (or weaker) water absorbing wavelength of 1300 nm, having a bandwidth of about 100 nm (FWHM) (model L1300-03, Epitex Inc., Kyoto, Japan). Hence, the spectra of the light beams emitted from these LEDs 52, 54 are separated from each other in order to provide a clear separation between water absorbing wavelength and non (or weaker) water absorbing wavelength. An InGaAs photodiode (model PD1300-35T00, Epitex Inc., Kyoto, Japan) serves as sensing element (IR-photodiode) 58 located in the lower housing 56 of the TIRWI-sensor, which is responsive within the 800-1700 nm range.

Both housings 52, 56 of the TIRWI-sensor, the upper housing 52 and the lower housing 56, are mounted on a tweezers like fixture, (not shown) such as the gripping fixture 24 of FIG. 1 in a way that the apertures 60 of both housings face each other. Since the tweezers fixture provides a closing force, this fixture can be clipped onto a plant leaf 26 so that the leaf 26 is located between the illuminating LEDs 52, 54, located in the upper sensor housing 50, and the sensing IR-photodiode 58, located in the lower sensor housing 56. Foam may be used in areas where the fixture touches the leaf in order to provide shielding from ambient light.

The illuminating LEDs 52, 54 and the sensing IR-photodiode 58 are connected to appropriate electronics (stand-alone or in conjunction with a computer or a computer alone), which turns the LEDs 52, 54 on and off in proper sequences and conducts the readout of the sensing IR-photodiode 58 at appropriate times. Therefore, if the fixture is clipped onto a leaf 26, and one of the LEDs 52, 54 is turned on, emitting light at its specific wavelength, this light will penetrate the leaf 26 under test. Some of this light will be transmitted through the leaf, emanating from the opposite side of this leaf, through the apertures 60, and may eventually be received by the sensing IR-photodiode 58.

Before measurements are to be taken from leaves, the electronics records and stores the incident photon fluxes of both LEDs ($I_{t\_0}$), that is the received photo flux from each LED without any plant leaf being present between the illuminating LEDs and the sensing IR-photodiode. During measurements, i.e. with plant leaves being present between the illuminating LEDs and the sensing IR-photodiode, the electronics records and stores the measured photon fluxes for each of the LEDs when they are turned on ($I_{t\_leaf}$) and calculates the transmittance (T) for each LED according to the formula:

$$T = I_{t\_leaf} / I_{t\_0}$$

thus yielding T1300 and T1450 values. The TIR-water index (TIRWI) is finally calculated by the formula:

TIRWI=$T1300/T1450$.

Method 4: The present method of measuring turgor pressure in plants utilizes the principle of "pressure broadening and shifting of spectral absorption bands".

The principle of pressure broadening describes the change of the shape of spectral absorption bands, or absorption lines, as a function of pressure applied towards an absorbing material. It is generally known that the width of absorption bands, or absorption lines, typically defined as the full width at half maximum (FWHM), increases if pressure increases. It has also been observed in numerous applications that the occurrence of the maximum of absorbance, or absorption band center wavelength, may shift to different wavelengths if pressure increases. These pressure changes can typically be observed for relatively small pressure changes in gases. In liquids and solids these effects can only be observed under at least one of two conditions: comparably large fluctuations of pressure or high spectral resolution of the measurement equipment.

Light transmitted through a plant leaf exhibits characteristic absorption bands, such as absorption bands caused by water, various types of chlorophyll, or other types of leaf pigments. The same is true for light reflected from leaves since light reflection occurs mainly at the interior of leaves, more specifically mostly at the layer of spongy mesophyll cells, hence reflected light has traveled through a leaf under test to quite some extent. The absorbing materials causing these various absorption bands are typically exposed to the pressure within leaf cells, which is the turgor pressure of leaf cells. Thus, the exact spectral occurrences of the absorption maxima of the above described absorption bands of water and leaf pigments, or absorption band center wavelengths, should be a function of the turgor pressure of the cells of a leaf under test. By measuring the spectrum of light reflected from or transmitted through leaves, by observing the exact spectral occurrence of the absorption maximum of certain absorption bands, and by applying the principle of pressure shifting of spectral absorption bands it is therefore theoretically possible to use this principle as a novel tool for measuring the turgor pressure of cells in plant leaves non-destructively and in real-time.

Figure 4:
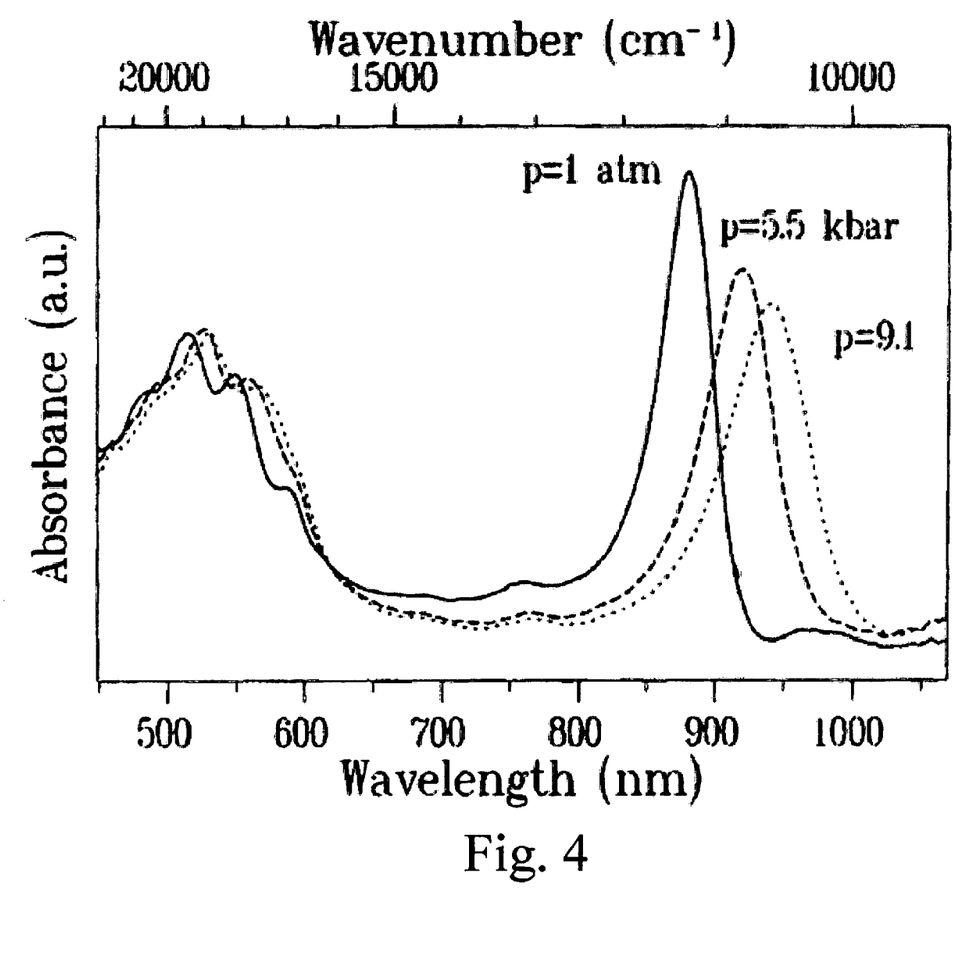
FIG. 4 is a graph showing the shift in wavelength of light due to the change of turgor pressure in purple bacteria *Rhodospirillum rubrum*.

Please refer to FIG. 4. The effect of pressure on the absorption characteristics of the light harvesting pigment protein complex (LHC) of membranes of the purple bacteria *Rhodosphirilum rubrum* at room temperature has been studied. Since the prepared protein complexes of this experiment were placed in water solution, these experiments resemble the natural environment of cells in plant leaves containing various protein complexes. When the absorbance from the above named solution was measured, the LHC exhibited a single absorption band in the very near infrared (VNIR) light range, centered at about 865 nm at ambient pressure of about one atmosphere (1 atm). When pressure higher than 1 atm was applied to this solution, the FWHM of the absorption band centered at 865 nm at 1 atm increased. More importantly, the center wavelength of this absorption band, i.e. the wavelength of maximum absorbance, shifted towards higher wavelength under pressure, and the observed shift of the absorption band center wavelength appeared to be a linear function of the pressure being applied.

The pressures applied were much higher compared to turgor pressures occurring naturally in plant leaves. The maximum values of turgor pressure in plant leaf cells are typically between about 0.5 MPa and about 2.0 MPa. Scaling the shift of the absorption band center wavelength down to natural turgor pressures in plant leaf cells yields a shift of the center wavelength of the above-described LHC absorption band of about 0.1 nm per MPa.

Each family of plant leaf pigments exhibits its own characteristic absorption spectra. When assessing light reflected from or transmitted through leaves, the absorption spectra of all pigment families involved overlap, creating an integrated absorption spectrum. Throughout the 400-500 nm range, different individual absorption bands overlap, creating high absorbance over this wavelength range without any clearly identifiable maximum of absorbance, so that this spectral range can likely not be used for the principle of pressure shifting of spectral absorption bands.

Within the 550-750 nm range, different individual absorption bands overlap as well. The observable integrated absorption spectrum throughout this range, however, does exhibit a clearly identifiable absorption maximum, usually occurring at about 650 nm, caused by absorption of leaf pigments, such as chlorophyll and carotenoids. The following evaluation examined the exact occurrence of this absorption maximum, i.e. the center wavelength of this absorption band. In preparation of this experiment, various peace lily (*Spathiphyllum lynise*) plants were subjected to various degrees of desiccation, creating a variety of leaf RWC. Spectral reflectance was measured using a spectroradiometer scanning the 350-2500 nm wavelength range (Field Spec Pro FR, Analytical Spectral Devices, Inc., Boulder, Colo.). Spectral resolution of this device was about 2 nm in the 350-1000 nm range, and about 5 nm in the 1000-2500 nm range. In order to calculate the center wavelength of the 650 nm absorption band, software written in Labview (National Instruments, Corp., Austin, Tex.) was fed with the obtained reflectance spectra. The software examined the 550-750 nm range only and determined throughout this range the wavelength at which minimum reflectance, i.e. maximum absorbance, occurred.

In the infrared (IR) range, leaf absorption by pigments becomes negligible and the five typically observable absorption bands throughout the 750-2500 nm wavelength range are caused by water exclusively. The following evaluation examined the occurrence of the absorption maximum of the 1450 nm absorption band using the same procedure as described above for the 650 nm absorption band. A dependency of the occurrence of the 650 nm leaf absorption band upon leaf dehydration may be observable for light reflected from leaves.

However, within the 350-1000 nm wavelength range the spectral resolution of the spectroradiometer used was only about 2 nm and within the 1000-2500 nm wavelength range the spectral resolution of the spectroradiometer used was only about 5 nm. Indeed, noise on the order of about 2-5 nm can be observed. Therefore, if the effect of pressure shifting of absorption bands indeed exhibits a sensitivity of only about 0.1 nm per MPa, as described by Freiberg et al. (1993), the spectroradiometer was too insensitive in terms of its spectral resolution to resolve the effect for natural turgor pressures of about 2.0 MPa maximum.

Therefore, the use of spectroradiometers, or other devices providing spectral separation such as spectrally tunable lasers, with higher spectral resolution than the spectroradiometer used in the experiments described above may be able to resolve the effect of pressure shifting of absorption bands as a way to measure turgor pressure of leaf cells much better. In particular, if such spectroradiometers or other devices would offer a spectral resolution of below 0.1 nm they may be able to resolve the effect of pressure shifting of absorption bands for natural changes of turgor pressure occurring in leaf cells.

The application of spectroradiometers or other devices exhibiting spectral resolution of below 0.1 nm is practically feasible. Examples for commercially available equipment already offering such high spectral resolution include the HR4000 high-resolution spectroradiometer of Ocean Optics offering a spectral resolution of about 0.02 nm with appropriate optical configuration (Ocean Optics, Inc., Dunedin, Fla.; Ocean Optics, 2004), miniature spectroradiometers known as optical channel monitors (OCM) typically used in telecommunication applications offering a spectral resolution of about 0.025 nm, or the varieties of spectrally tunable lasers, such as the ECL5000DT tunable laser of THORLABS offering a spectral resolution of 0.001 nm (spectral line width 150 kHz FWHM) (THORLABS, Inc., Newton, N.J.; THORLABS, 2005).

In addition to the use of spectroradiometers or other devices with high spectral resolution of below 0.1 nm, mathematical procedures could be used in order to increase the spectral resolution of the method for measuring turgor pressure in leaf cells using the principle of spectral shifting of absorption bands virtually. So far, the method described here determined the occurrence of maximum absorbance, or absorbance band center wavelength, by feeding software with the obtained spectrum of interest, and the software would determine the occurrence of maximum absorbance by determining the wavelength at which, for example, minimum reflectance, i.e. maximum absorbance, of an absorption band of interest occurs. Clearly, such a procedure is limited in its spectral resolution to the spectral resolution of the spectrum obtained, i.e. is limited to the spectral resolution of the spectroradiometer, or other device, used for obtaining the spectrum. In order to increase spectral resolution virtually one could apply mathematical curve fitting procedures to the spectrum obtained. This way, the set of real data of the spectrum with its limited spectral resolution is replaced with an exact mathematical model, or function, of the obtained absorption band. The mathematical function, of course, offers a much higher theoretical spectral resolution compared to the set of real data of the spectrum obtained. Differentiating the mathematical function of the absorption band and solving this differentiated function for zero calculates an exact wavelength at which maximum absorption of the absorption band examined occurred. With this procedure the spectral resolution of determining the occurrence of absorption maximum of an absorption band can virtually be increased extremely. The limiting factor of this procedure is "how good the mathematical function can be fitted to the set of real data". However, applying well fitting mathematical functions to the real sets of data of absorption bands promises to increase the spectral resolution substantially when determining the exact occurrence of absorption band maxima.

Furthermore, it was noticed earlier that the true independent variable for the principle of pressure shifting of spectral absorption bands is the change in density of the absorbing material. The density of materials, however, depends on the pressure being applied and the temperature. In fact, temperature may have a much larger impact on changes in the density of water than pressure does. Thus, temperature fluctuations may influence the shift of spectral absorption bands in the same way as pressure fluctuations would. Therefore, the temperature of the absorbing material, in the case of turgor pressure in leaf cells the temperature of leaves under test, need to be measured and taken into account when determining the turgor pressure of leaf cells using the principle of pressure shifting of spectral absorption bands. Alternatively, the temperature of the absorbing material, in the case of measuring the turgor pressure of leaf cells the temperature of the leaf under test, may be actively controlled to a certain defined temperature, and kept constant throughout the measurement, which would eliminate the influence of temperature leaving turgor pressure to be the only contributor to influence the shift of spectral absorption bands when measuring light reflected from or transmitted through plant leaves.

The present invention provides a method of determining the turgor pressure in a plant by shining light through a leaf or measuring the light reflected from the leaf; spectrally examining typical absorption bands of chlorophyll, other pigments, or water; determine the turgor pressure inside the leaf based on the senter-wavelength of the absorption bands.

Spectral examination can be done by using a broad light emitting source and a spectrometer as the receiving element, or using a spectrally tunable laser and a simple spectrally broad receiving element such as a photodiode, for example.

Although this invention has been described with respect to specific embodiments, it is not intended to be limited thereto and various modifications which will become apparent to the person of ordinary skill in the art are intended to fall within the spirit and scope of the invention as described herein taken in conjunction with the accompanying drawings and the appended claims.

The invention claimed is:

1. A method of detecting plant water deficit stress in plants by measuring plant leaf thickness using a Hall Effect Sensor and using this measurement to determine a level of water deficit in plants, the method comprising:
   a) mounting a Hall Effect Sensor Integrated Circuit on the first arm of a gripper like fixture;
   b) mounting a magnet on the second arm of a gripper like fixer; wherein said mounting permits the arms to touch opposite sides of a leaf to be measured;
   c) measuring the magnetic flux density;
   d) converting the measured magnetic flux density into a corresponding voltage;
   e) comparing the voltage of step d) to voltage measured when no leaf is present;
   f) determining leaf thickness by comparing the voltages; and
   g) determining a level of water deficit stress in plants using the determined leaf thickness by comparing the voltages.

2. The method according to claim 1 further comprising communicating said measurement to a user wherein communicating can be selected from the group consisting of: conversion of data into human voice, transmission of data over the Internet to other computers, PDAs or cell phones, transmission of information to pagers, and the transmission of information to cell phones, wherein information is in the form of digital data or human voice.

3. A plant leaf thickness sensor comprising:
   a) Hall Effect Sensor Integrated Circuit mounted on the first arm of a gripper like fixture;
   b) at least one magnet mounted on the second arm of a gripper like fixture; wherein said mounting permits the arms to touch opposite sides of a leaf to be measured;
   c) fixture having a first arm and a second arm for gripping a leaf
   d) means for measuring the magnetic flux density;
   e) means for converting the measured magnetic flux density into a corresponding voltage;
   f) means for comparing the voltage of step e) to voltage measured when no leaf is present and
   g) determining leaf thickness by comparing the voltages.

* * * * *